(12) United States Patent
McKinney et al.

(10) Patent No.: US 11,984,206 B2
(45) Date of Patent: May 14, 2024

(54) AUTOMATED EXTRACTION OF STRUCTURED LABELS FROM MEDICAL TEXT USING DEEP CONVOLUTIONAL NETWORKS AND USE THEREOF TO TRAIN A COMPUTER VISION MODEL

(71) Applicant: GOOGLE LLC, Mountain View, CA (US)

(72) Inventors: Scott McKinney, Mountain View, CA (US); Shravya Shetty, Mountain View, CA (US); Hormuz Mostofi, Mountain View, CA (US)

(73) Assignee: Google LLC, Mountain View, CA (US)

( * ) Notice: Subject to any disclaimer, the term of this patent is extended or adjusted under 35 U.S.C. 154(b) by 557 days.

(21) Appl. No.: 16/958,544

(22) PCT Filed: Feb. 16, 2018

(86) PCT No.: PCT/US2018/018509
§ 371 (c)(1),
(2) Date: Jun. 26, 2020

(87) PCT Pub. No.: WO2019/160557
PCT Pub. Date: Aug. 22, 2019

(65) Prior Publication Data
US 2021/0065859 A1     Mar. 4, 2021

(51) Int. Cl.
*G16H 15/00*     (2018.01)
*G06N 3/08*      (2023.01)
*G16H 30/40*     (2018.01)

(52) U.S. Cl.
CPC .............. *G16H 15/00* (2018.01); *G06N 3/08* (2013.01); *G16H 30/40* (2018.01)

(58) Field of Classification Search
CPC ........... G16H 15/00; G16H 30/40; G06N 3/08
See application file for complete search history.

(56) References Cited

U.S. PATENT DOCUMENTS 6,011,862 A   1/2000  Doi et al.
6,058,322 A   5/2000  Nishikawa et al.
(Continued)

FOREIGN PATENT DOCUMENTS

CN      106484674 A     3/2017
WO      2016/057960     4/2016
(Continued)

OTHER PUBLICATIONS

Linnan Wang et al., Accelerating deep neural network training with inconsistent stochastic gradient descent, Jun. 16, 2017, Neural Networks 93 (2017), pp. 219-229 (Year: 2017).*

(Continued)

*Primary Examiner* — Robert A Sorey
*Assistant Examiner* — Kimberly A. Sass
(74) *Attorney, Agent, or Firm* — McDonnell Boehnen Hulbert & Berghoff LLP (57) ABSTRACT

A method is provided for processing medical text and associated medical images. A natural language processor configured as a deep conventional neural network is trained on a first corpus of curated free-text, medical reports each of which having one or more structured labels assigned by an medical expert. The network is trained to learn to read additional free-text medical reports and produce predicted structured labels. The natural language processor is applied to a second corpus of free-text medical reports that are associated with medical images. The natural language processor generates structured labels for the associated medical images. A computer vision model is trained using the medical images and the structured labels generated. The computer vision model can thereafter assign a structured label to a further input medical image. In one example, the medical images are chest X-rays.

21 Claims, 7 Drawing Sheets

(56) References Cited

U.S. PATENT DOCUMENTS

| | | | |
|---|---|---|---|
| 6,125,194 A | 9/2000 | Yeh et al. | |
| 6,760,468 B1 | 7/2004 | Yeh et al. | |
| 7,912,528 B2* | 3/2011 | Krishnan | G16H 50/20 600/407 |
| 7,949,167 B2 | 5/2011 | Krishnan et al. | |
| 9,589,374 B1 | 3/2017 | Gao et al. | |
| 10,679,345 B2* | 6/2020 | Madani | G06N 3/044 |
| 2016/0321427 A1 | 11/2016 | Bogoni et al. | |
| 2018/0032902 A1* | 2/2018 | Krishnan | G06N 20/00 |
| 2018/0342060 A1* | 11/2018 | Yao | G16H 40/63 |

FOREIGN PATENT DOCUMENTS

| | | |
|---|---|---|
| WO | 2016/094330 | 6/2016 |
| WO | 2017/151757 | 9/2017 |
| WO | 2017/152121 | 9/2017 |
| WO | 2018/011432 | 1/2018 |

OTHER PUBLICATIONS

The International Search Report (ISR) with Written Opinion for PCT!US2018/018509 dated Sep. 18, 2018, pp. 1-18.

Wang, Xiaosong et al. "ChestX-ray8: Hospital-scale Chest X-ray Database and Benchmarks on Weakly-Supervised Classification and Localization of Common Thorax Diseases" {xiaosong.wang,yifan.peng,le.lu,luzh,mohammad.bagheri,rms}@nih.gov; arXiv.org.cs. arXiv:1705.02315 (2017).

Chen, Matthew C. et al. "Deep Learning to Classify Radiology Free-Text Reports" Radiology (2018) vol. 286(3), pp. 845-852.

\* cited by examiner

Token attribution via *Integrated* Gradients $IG_i(image) = image_i * \int_{0-1} \nabla F_i(\alpha * image) \, d\alpha$ where:
- F is the prediction function for the label
- $image_i$ is the RGB intensity of the $i^{th}$ pixel
- $IG_i(image)$ is the integrated gradient w.r.t. the $i^{th}$ pixel, i.e., attribution for $i^{th}$ pixel

AUTOMATED EXTRACTION OF STRUCTURED LABELS FROM MEDICAL TEXT USING DEEP CONVOLUTIONAL NETWORKS AND USE THEREOF TO TRAIN A COMPUTER VISION MODEL

CROSS REFERENCE TO RELATED APPLICATIONS

The present application claims priority as a U.S. national stage entry of PCT application serial no. PCT/U2018/018509 filed 16 Feb. 2018. The full disclosure of PCT/U2018/018509 is incorporated herein by reference.

BACKGROUND

Medical opinions and observations are typically communicated in the form of a natural language, free-text report prepared by a physician. Such unstructured text, ubiquitous in medical records, can create great difficulty for downstream consumers of this information. Healthcare providers maintain massive archives of medical reports, but it is difficult to harness the full potential due of such reports due to the poor standardization of medical notes.

Unstructured medical notes pose challenges in many situations:
1. Retrieving cases of interest for review and research (e.g. identifying all patients with a rare disease).
2. Rapidly appreciating the preexisting conditions afflicting a patient before administering care. Reading many long-winded reports can be time consuming and error-prone.
3. The development of automated tools to support medical decision making. Most artificial intelligence techniques require structured data.
4. Quality monitoring, e.g. determining how often patients with condition X receive treatment Y.
5. Billing. In most healthcare systems a medical encounter must be translated into a standard set of codes to be eligible for reimbursement.

In use case (1), a clinician or researcher seeks to identify from a large hospital archive the records of patients afflicted with a particular condition, say, or patients who received a particular form of treatment. This might be for recruiting subjects to participate in a clinical trial based on eligibility criteria, or for educational/training purposes. This task is incredibly painstaking without a database of structured clinical variables against which to query. Simple string matching of the text notes can have very poor specificity. And later, medical personnel must comb through each record to determine if a particular condition was affirmed.

In use case (2), a healthcare provider seeks to absorb a patient's history at first encounter. A patient may have been in the healthcare system for quite a while; to effectively treat the patient they must gain an understanding of prior encounters based on scattered notes written by numerous providers (hospitalists, radiologists and other specialists.) This can be time-consuming and error-prone when there are many documents to review. An automated system that surfaces concrete clinical variables based on prior documents and draws the reader's attention to relevant portions of a longer note could save valuable time in the clinic.

Research in medical informatics often seeks to replicate the judgments of a human expert through automated systems. Such efforts often rely on retrospective data comprising many instances of patient information (e.g. lab tests, medical images) paired with diagnoses, treatment decisions, or survival data. In the paradigm of supervised learning, the patient data are the "inputs", while the diagnoses, outcomes, or treatment recommendations are the "outputs". The modeling task is then to learn to predict this information given access to the patient record from an earlier point in time. For instance, an application of computer vision might seek to automatically determine what is causing a patient's chest pain by inspecting an X-ray image of the patient's chest. Such a system would be trained by leveraging previously captured images and the corresponding opinions of their radiologists.

For training and evaluating these models, it is important to have highly structured outputs on which clinically significant metrics can be defined. An example of a highly structured output would be the code of the medication that was subsequently prescribed. In many areas of medicine (e.g. radiology, pathology) the "inputs" to a diagnostic system are consistently archived as digital images, and are thus amenable to modern machine learning methods. Lamentably, historical diagnoses (our "outputs") are almost always sequestered among natural language rendered by the physician. This text is often unstructured and poorly standardized, and thus difficult to use in the context of machine learning. Recasting this information using a standardized schema or rubric requires a great deal of effort from medical personnel, and is thus a time-consuming and costly effort.

SUMMARY

This disclosure relates to a method of generating structured labels for free-text medical reports, such as doctor notes, and associating such labels with medical images, such as chest X-rays which are adjunct to the medical reports. This disclosure also relates to a computer vision system which classifies or generates structured labels from input image pixels alone. This computer vision model can assist in diagnosis or evaluation of medical images, for example chest X-rays.

In this document, the term "structured labels" refers to data according to a predetermined schema, or in other words a standardized format. The data is for conveying diagnostic or medical condition information for a particular sample (e.g., free-text report, associated image or image alone). One example of a structured label is a set of one or more binary values, for example positive (1) or negative (0) for a medical condition or diagnosis, such as pneumothorax (collapsed lung), pulmonary embolism, misplaced gastric feeding tube, etc. in the context of a chest X-ray or associated medical report. Alternatively, the structured labels could be a schema or format in the form of a set of one or more binary values for the assignment of a diagnostic billing code, e.g., "1" meaning that a particular diagnostic billing code for pulmonary embolism should be assigned, "0" meaning that such code should not be assigned. The particular schema will depend on the application, but in the example of chest X-rays and associated medical reports, it can consist of a set of binary values to indicate presence or absence of one or more of the following conditions: airspace opacity (including atelectasis and consolidation), pulmonary edema, pleural effusion, pneumothorax, cardiomegaly, nodule or mass, misplaced nasogastric tube, misplaced endotracheal tube, misplaced central venous catheter, and presence of chest tube. In addition, each of these conditions might have binary modifiers such as laterality (e.g., 1 for left, 0 one for right) or severity. The structured label may also include a severity term, in one possible example it could a binary modifier that may be 1, 2 or 3 bits of information in the structured label in order to encode different values of severity. Or, as another example, the structured label could encode some rubric or schema for severity such some integer value, e.g., absent=0, mild=1, moderate=2, severe=3, or a severity scale from 1 to 10.

For example, a structured label for a given medical report, or for a given medical image, could take the form of [100101] where each bit in the label is associated with a positive or negative finding of a particular medical condition, billing code, or diagnosis, and in this example there are six different possible findings or billing codes for this example. The structured labels can be categorical as well as binary. For example, a model can produce a label in the set {absent, mild, moderate, severe} or some numerical equivalent thereof.

The method uses a natural language processor (NLP) in the form of a one-dimensional deep convolutional neural network trained on a curated corpus of medical reports with structured labels assigned by medical specialists. This NLP learns to read free-text medical reports and produce predicted structured labels for such reports. The NLP is validated on a set of reports and associated structured labels to which the model was not previously exposed.

The NLP is then applied to a corpus of medical reports (free-text) for which there are associated medical images such as chest X-rays but no clinical variables or structured labels of interest which are available. The output of the NLP is the structured label associated with each medical image.

The medical images with the structured labels assigned by the NLP are then used to train a computer vision model (for example, a deep convolutional neural network pattern recognizer) to assign or replicate the structured labels to medical images based on image pixels alone. The computer vision model thus functions essentially as a radiologist (or, more typically, as an intelligent assistant to a radiologist) producing a structured output or label for a medical image such as a chest X-ray, instead of a natural language or free-text report.

In one possible embodiment, the methodology includes a technique or algorithm, known as Integrated Gradients, implemented as a software module which assigns attribution to the words or phrases in the medical reports which contributed to the assignment of the structured label to the associated images(s). The methodology allows such attributions to be represented to a user for example by showing excerpts from the medical report with pertinent terms highlighted. This has tremendous applicability in the healthcare context where providers typically sift through long patient records to find information of interest. For example, if the NLP identifies that the medial image shows signs of a cancerous lesion, the relevant text in the associated report can be highlighted.

In one configuration of this disclosure, there is described a system for processing medical text and associated medical images. The system includes (a) a computer memory storing a first corpus of curated free-text medical reports each of which having one or more structured labels assigned by a medical expert; (b) a natural language processor (NLP) configured as a deep convolutional neural network trained on the first corpus of curated free-text medical reports to learn to read additional free-text medical reports and produce predicted structured labels for such additional free-text medical reports; and (c) a computer memory storing a second corpus of free-text medical reports (and which are typically without structured labels) that are associated with medical images. The NLP is applied to such second corpus of free-text medical reports and responsively generates structured labels for the associated medical images. The system further includes (d) a computer vision model which is trained on the medical images and the structured labels generated by the NLP. The computer vision model operates (i.e., performs inference) to assign a structured label to a further input medical image, e.g. a chest X-ray for which there is no associated free-text medical report. In this manner, the computer vision model functions as an expert system to read medical images and generate structured labels, like a radiologist or as an assistant to a radiologist. The NLP and the computer vision model are typically implemented in special purpose computers configured with hardware and software for implementing deep learning models as is customary in the art.

In one embodiment the computer vision model and NLP are trained in an ensemble manner as will be apparent from the following description.

In one possible configuration, the system includes a module implementing an Integrated Gradients algorithm assigning attribution to input words in the free-text medical reports to the structured label generated by the NLP. The system may further include a workstation having a display for displaying both the medical images, free-text reports, and the attribution to elements in the report calculated by the Integrated Gradients algorithm.

As will be explained below, in one embodiment the medical images are chest X-rays. The computer vision model is trained to generate structured labels for a chest X-ray based on the image pixels alone, and without requiring an associated free-text medical report. The structured labels can for example be a series binary values indicating positive or negative for particular findings or diagnostic billing codes, optionally including laterality or severity, as explained above.

In a further aspect of the disclosure there is provided a method for processing medical text and associated medical images comprising:

training a natural language processor on a first corpus of free-text medical reports each of which having one or more structured labels assigned by an medical expert, the natural language processor trained to learn to read additional free-text medical reports and produce predicted structured labels for such additional free-text medical reports;

applying the natural language processor to a second corpus of free-text medical reports without structured labels that are associated with medical images and wherein the natural language processor generates structured labels for the associated medical images; and training a computer vision model using the medical images and the structured labels generated by the natural language processor to assign a structured label to a further input medical image.

In a further aspect of the invention there is provided a machine learning system comprising, in combination, a computer memory storing a set of training data in the form of a multitude of training examples, each of which comprises a free-text medical report and one or more associated medical images, wherein a subset of the training examples contain ground truth structured labels assigned by a medical expert; and a computer system configured to operate on each of the multitude of training examples, and wherein the computer system is configured as a) a feature extractor receiving as input the one or more medical images and generating a vector of extracted image features from the one or more medical images;

b) a diagnosis extraction network receiving as input a free-text medical report and the vector of extracted image features and generating a structured label;

c) an image classifier trained on vectors of extracted features produced by the feature extractor from one or more medical images of the multitude of training examples and corresponding structured labels; wherein the image classifier is further configured to generate a structured label for a further input medical image from a feature vector generated by the feature extractor from the further input medical image.

The term "curated" is used to mean that a corpus of data includes at least some elements generated by human intelligence, such as the structured labels assigned by the medical expert during training.

DETAILED DESCRIPTION

In one aspect, the work described in this document relates to a methodology of developing a computer vision model, typically embodied in a computer system including memory and processor functions, and consisting of certain algorithms, which is capable of emulating a human expert's interpretation of medical images. To build such a model we follow the highly successful paradigm of supervised learning: use many examples of radiology images (the input) paired with a corresponding set of findings generated by a radiologist (the outputs) to train a deep learning computer vision model to replicate the specialist's diagnostic process. The goal is that if we train on enough data, from enough doctors, our model can perhaps surpass human performance in some domains.

Figure 1:
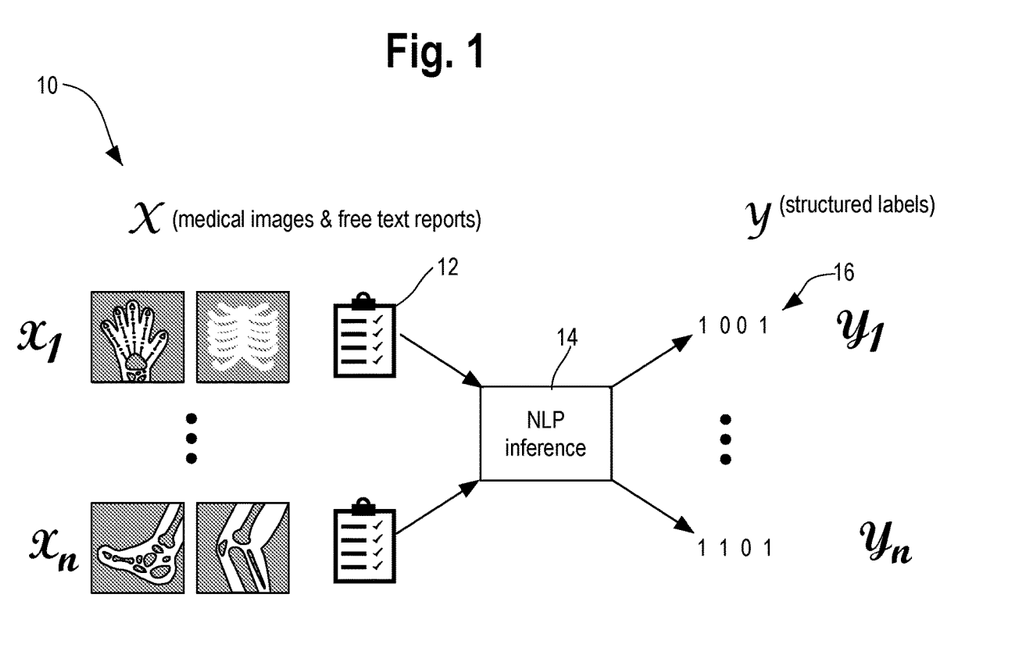
FIG. 1 is an illustration of a machine learning process for generating structured labels for sets of medical images and associated free-text medical reports.

FIG. 1 is an illustration of a machine learning process for generating structured labels for sets of medical images and associated free-text medical reports which will explain the motivation of this disclosure. The goal in this context is to generate a machine learning model 14 that can use as input (X) one or more medical images 10 and a free text report 12 associated with the medical images and produce an output (Y) in the form of a structured label 16. For each input $X_1 \ldots X_N$ the model 14 generates an output $Y_1 \ldots Y_N$. The model 14 is shown as having two components, natural language processing (NLP) applied to the text component and inference (pattern recognizer) which is applied to the medical images.

Lamentably, in most medical clinics, radiologists transmit their opinions back to the referring physician in the form of unstructured, natural language text reports of a few hundred words. Thus, while the inputs to our computer vision model—radiological images—are consistently archived in digital format and require little preprocessing, the outputs—i.e. the medical diagnoses, or findings, or equivalently structured labels which the computer vision model should replicate—are sequestered among unstructured, poorly standardized natural language.

Although frameworks exist for translating images directly into strings of text, our application demands a more structured output, i.e., the labels 16 of FIG. 1, on which clinically significant metrics can be defined. One approach to this problem might be to recruit radiologists to revisit historical scans and annotate them using a structured form. However, to attempt to meet the data requirements of a state-of-the-art computer vision model in this fashion would be slow, costly and wasteful—considering all of these scans have already been interpreted. Hence, this disclosure provides for a more efficient and cost effective approach to generating the structured labels and in turn training a computer vision model.

An automated system that can extract structured data (labels 16 of FIG. 1) from a free-text radiology report, as described in this document, unlocks troves of training data for our computer vision model and associated algorithms. Investing in such a system by collecting human-labeled data expressly for this purpose, rather than collecting fresh image-based labels for training, would be extremely high-leverage. The annotation task is several times faster per case and can be performed by less specialized people. Plus, once a natural language processing model is trained, it can be applied to an arbitrary number of cases, yielding practically endless training data for a computer vision model.

Figure 2:
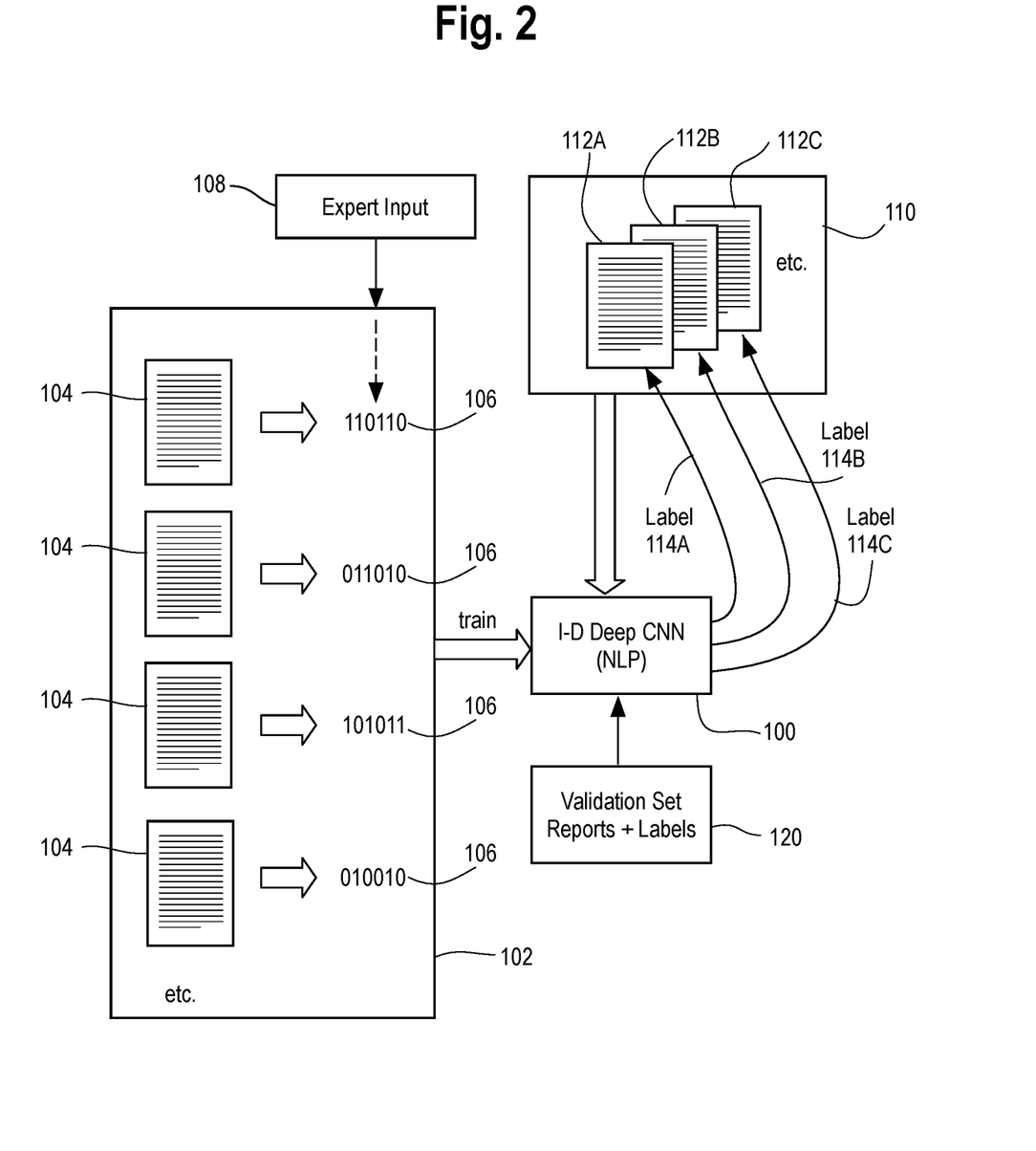
FIG. 2 is an illustration of a process for developing a natural language processor (NLP) in the form of a deep convolutional neural network by training it on a corpus of curated free-text medical reports; the neutral network learns to read additional free-text medical reports and produce predicted structured labels for such additional free-text medical reports.

Accordingly, one aspect of this disclosure relates to a method of generating structured labels for free-text medical reports, such as doctor notes, and associating such labels with medical images, such as chest X-rays which are adjunct to the medical reports. Referring now to FIG. 2, the method uses a natural language processor (NLP) 100 in the form of a one-dimensional deep convolutional neural network which is trained on a curated corpus of medical reports 102 consisting of a multitude of individual free text reports 104 each of which is associated with respective structured labels 106 which were assigned by a medical specialists (i.e., human experts). This input by experts is shown at 108 and could take for example one or more medical experts using a workstation to review the reports 104 and using an interface of the workstation assigning one or more binary values to various diagnostic or medical conditions which in their judgment are present in the patient associated with the report in a form-type document, for example a label such as [110110] where each bit is associating with positive or negative for a particular medical condition, diagnostic billing code, etc., as explained earlier. Additionally, the label may include bits or alphanumeric data to reflect laterality or severity as explained earlier.

This NLP 100 learns from the training corpus 102 to read free-text medical reports and produce predicted structured labels for such reports. For example, after this network has been trained it can be applied to a set 110 of free text reports and for each report 112A, 112B and 112C it generates a structured label 114A, 114B and 114C respectively. Additionally, this NLP 100 is validated on a set of reports and associated structured labels (FIG. 2, 120) to which the model was not previously exposed. Background information on machine learning methods for generating labels from text reports is described in Chen et al., *Deep Learning to Classify Radiology Free-Text Reports*, Radiology November 2017, the content of which is incorporated by reference herein. The scientific literature includes various descriptions of convolutional neural networks for text classification which may be suitable for use in this context, for example Yoon Kim, *Convolutional Neural Networks for Sentence Classification*, https://arxiv.org/pdf/1408.5882.pdf, and Ye Zhang et al., *A Sensitivity Analysis of (and Practitioners' Guide to) Convolutional Neural Networks for Sentence Classification* https://arxiv.org/pdf/1510.03820.pdf, and Alexis Conneau et al., *Very Deep Convolutional Networks for Text Classification*, arXiv:1606.01781 [cs.CL] (January 2017) and therefore a more detailed description of the NLP 100 is omitted for the sake of brevity.

Figure 3:
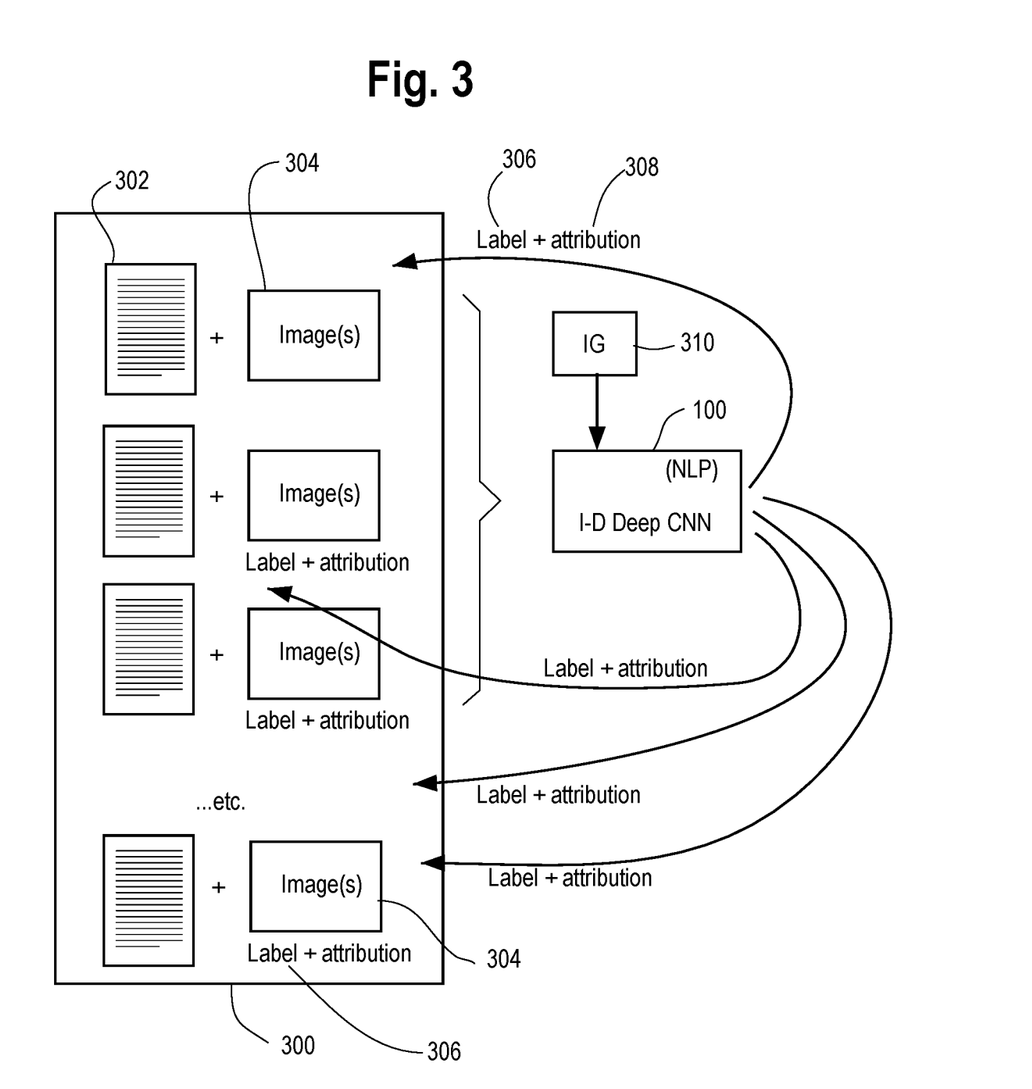
FIG. 3 is process of using the NLP of FIG. 2 to generate structured labels and attributions for free-text medical reports which are associated with one or more medical images.

Referring now to FIG. 3, the NLP 100 trained in accordance with FIG. 2 is then applied to a corpus 300 of medical reports (free-text) 302, each of which is associated with one or more medical images 304, such as for example chest X-rays but for which no structured labels encoding clinical variables of interest are available. The NLP's output is a structured label 304 which is associated with each image.

For example, the NLP 100 may have as input a free text report 302 indicating the presence of a misplaced gastric feeding tube, and an associated chest X-ray showing such a condition. The network has been trained from FIG. 2 to generate a label for misplaced gastric feeding tube (e.g., a label such as [100000] where the 1 indicates misplaced gastric feeding tube and the 0s indicate absence of other conditions), and this label [100000] is assigned to the associated chest X-ray.

The generation of structured labels from free text reports and assigning them to associated medical images allows for the generation of a large body of medical images which have assigned structured labels automatically. We previously noted it would in theory be possible to recruit radiologists to revisit historical scans and annotate them using a structured form. However, to attempt to meet the data requirements of a state-of-the-art computer vision model in this fashion would be slow, costly and wasteful—considering all of these scans have already been interpreted. Instead, using the training procedure of FIG. 2 and the labeling procedure of FIG. 3, we generate the structured labels for medical images automatically and without requiring vast amounts of time from trained radiologists.

In one embodiment, our methodology includes a technique, known as Integrated Gradients, which assigns attribution to the words or phrases in the medical reports which contributed to the assignment of the label to the associated image in FIG. 3. In particular, we use a software module 310 implementing an Integrated Gradients algorithm which generates weight or attribution to particular words or strings of words in the medical reports which contributed significantly to the label generation. This method is conceptually similar to "attention mechanisms" in machine learning. The output of the software module 310 is shown as the attribution 308. Our methodology allows such attributions to be represented to a user for example by showing excerpts from the medical report with pertinent terms highlighted, See FIGS. 5 and 6 discussed below. This has tremendous applicability in the healthcare context where providers typically sift through long patient records to find information of interest. For example, if the model identifies that the medial image shows signs of a cancerous lesion, the relevant text in the associated report can be highlighted. Integrated Gradients has been described as having applications in object recognition, diabetic retinopathy prediction, question classification, and machine translation, but its application in this context (attribution of text elements to binary classification of medical images) is new.

Figure 4:
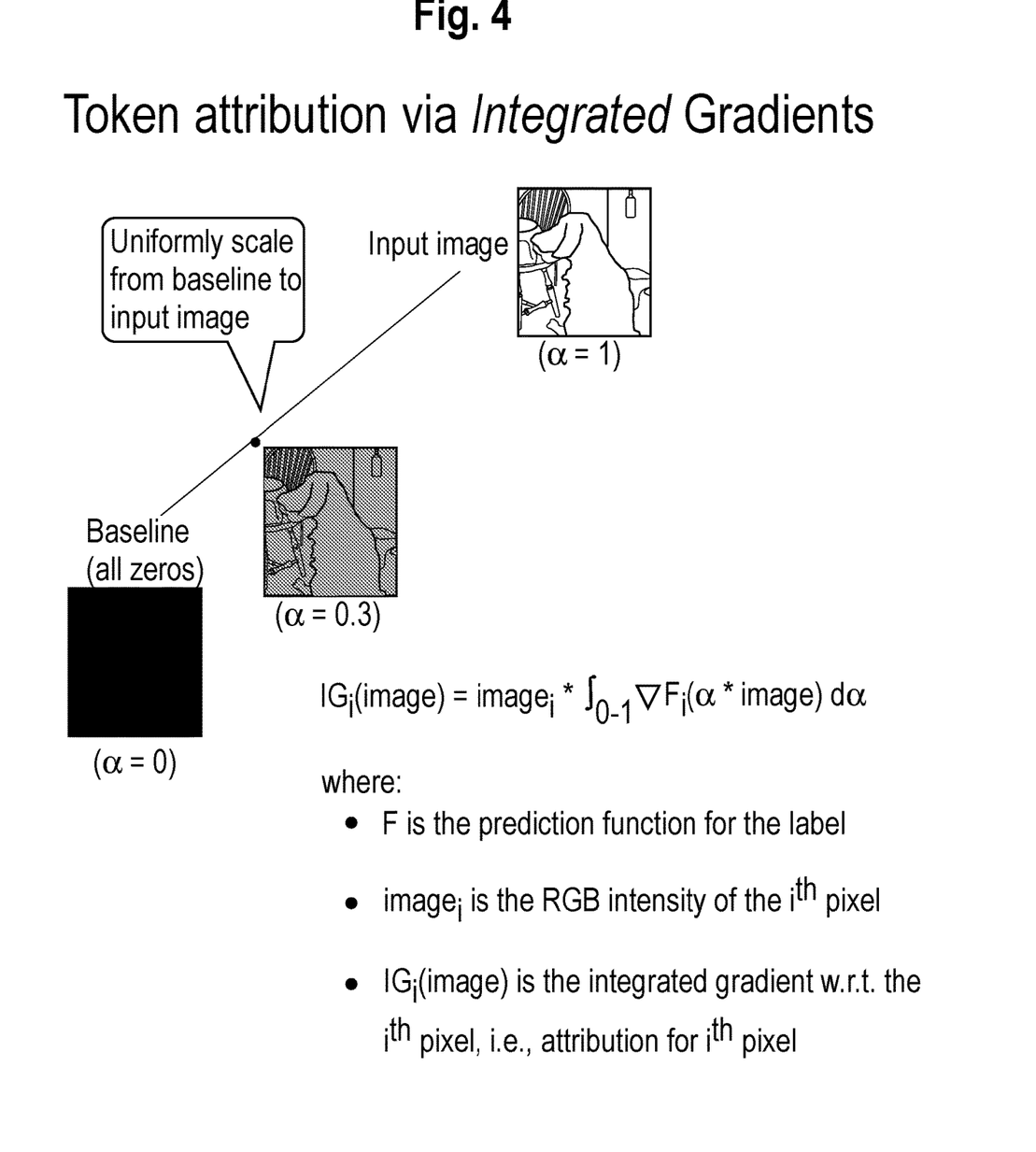
FIG. 4 is an illustration of a method known as Integrated Gradients which generates attribution for input tokens; while the illustration is shown for token attribution for pixels in an input image the method is performed analogously for token attribution where the input is words in free-text medical reports.

The Integrated Gradients algorithm is described in the paper of M, Sundararajan et al., *Axiomatic Attribution for Deep Networks*, arXiv:1703.01365 [cs.LG] (June 2017), the entire content of which is incorporated by reference. The methodology will be described conceptually in FIG. 4 in the context of attribution of individual pixels in an image in a classification of the overall image, and it applies by analogy to individual words in a free-text medical report. Basically, as shown in FIG. 4, an Integrated Gradients score $IG_i$ (or attribution weight or value) for each pixel i in the image is calculated over a uniform scaling ($\alpha$) of the input image information content (spectrum of brightness in this example) from a baseline (zero information, every pixel black, $\alpha=0$), to the full information in the input image ($\alpha=1$), where $IG_i$ (score for each pixel) is given by equation (1)

$$IG_i(\text{image}) = \text{image}_i * \int_{0-1} \nabla F_i(\alpha * \text{image}) d\alpha \qquad (1)$$

where F is a prediction function for the label;
$\text{image}_i$ is the RGB intensity of the ith pixel;
$IG_i$ (image) is the integrated gradient w.r.t. the $i_{th}$ pixel, i.e., attribution for $i_{th}$ pixel; and
$\nabla$ is the gradients operator with respect to $\text{image}_i$.

In the context of a free text medical report, the report is a one dimensional string of words of length L, and each word is represented as a, for example, 128 dimensional vector x in semantic space. The dimensions of the semantic space encode information of semantics, co-occurrence statistics of the presence or frequency of a word with other words, and other information content. $\alpha=0$ means each word in the report has no semantic content and no meaning (or could be represented as a zero vector) and as a goes to 1 each word goes to its full semantic meaning.

A more general expression of the Integrated Gradients is $$IntegratedGrads_i(x) ::= (x_i - x_i') \times \int_{\alpha=0}^{1} \frac{\partial F(x' + \alpha(x - x'))}{\partial x_i} d\alpha \qquad (2)$$

where the integrated gradient along the $i^{th}$ dimension for an input x and baseline x' is defined per equation (2). Here, $\partial F(x)/\partial xi$ is the gradient of $F(x)$ along the $i^{th}$ dimension. Section 3 of the Sundararajan et al. paper explain the algorithm further and that description is incorporated by reference. The gradient with respect to each word vector is itself a 128-dimensional word vector. Note that the number 128 is somewhat arbitrary, but not an uncommon choice. To get the final Integrated Gradients value for each word, the components are summed. Their sign is retained, so that net positive scores imply an attribution toward the positive class (with value 1) while net negative scores imply an attribution toward the negative or "absent" class (with value 0).

Figure 5:
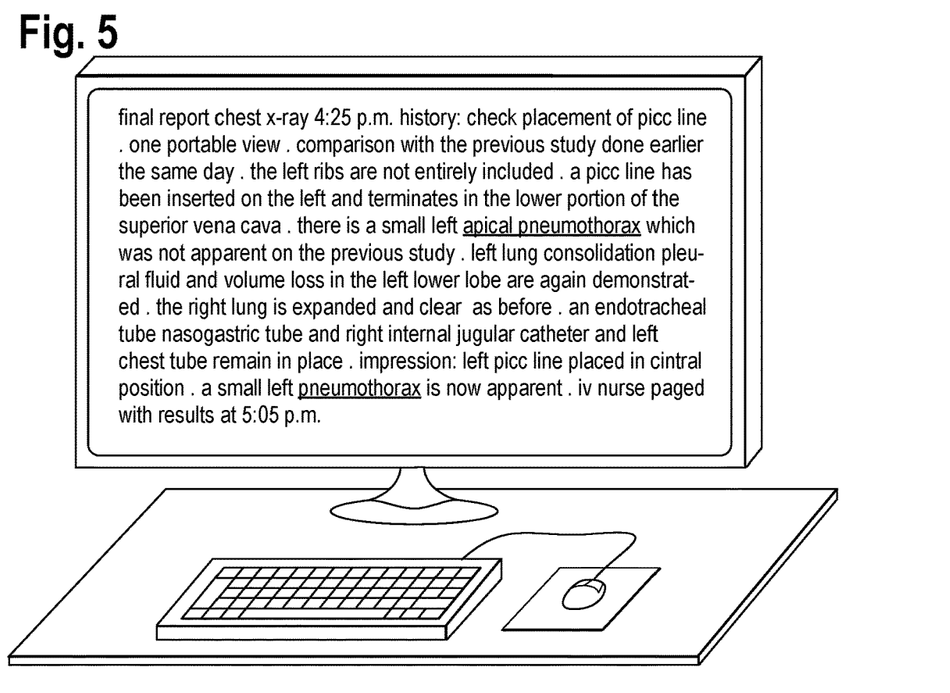
FIGS. 5 and 6 are illustrations of a display on a workstation in which text elements (words) in a free-text medical report which have high attribution for a generated structured label as shown in FIG. 3 are shown highlighted.
Figure 6:
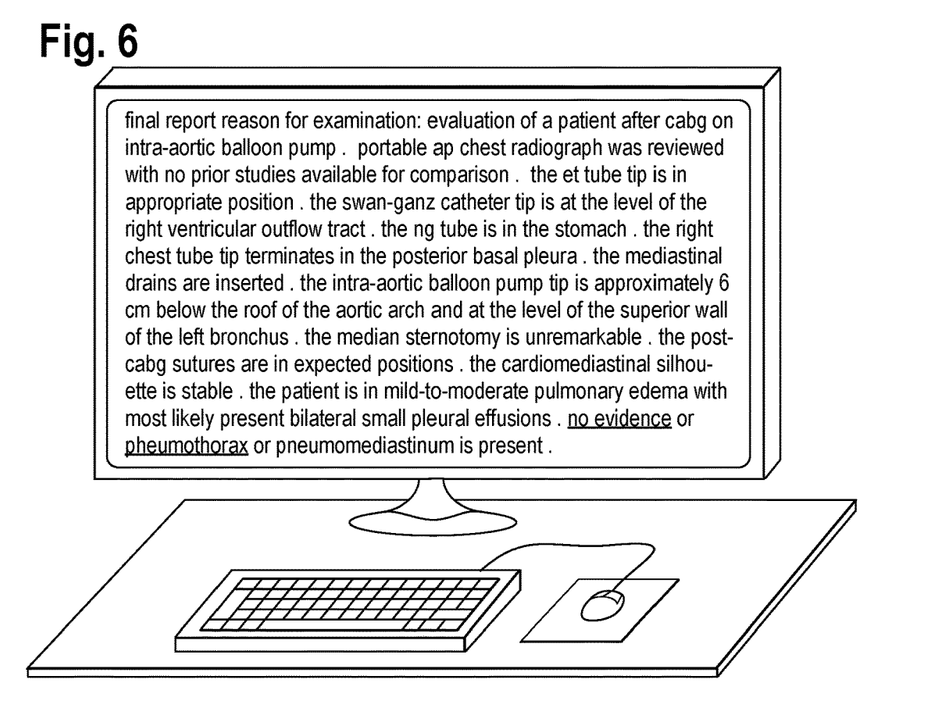

Just as the Integrated Gradients algorithm calculates the attribution value $IG_i$ for each pixel in the image example of FIG. 4, it calculates the attribution value for each word in the free text report 302 related to the label assigned to the associated image 304. In one possible configuration, the free text report can be displayed on a workstation as shown in FIGS. 5 and 6, along with a thumbnail of the associated image(s), and the free text report is color coded or highlighted in any suitable manner to bring the user's attention to the key words or phrases that had the highest attribution value scores and thereby assist the user in understanding why the label was assigned to the associated image. For example, all words in the report with a attribution score above a certain threshold (which could possibly by user-specified) is shown in bold font, red color, larger font size, underlined, or in some other Fashion to indicate that these words were the most significant in generating the structured label.

Figure 7:
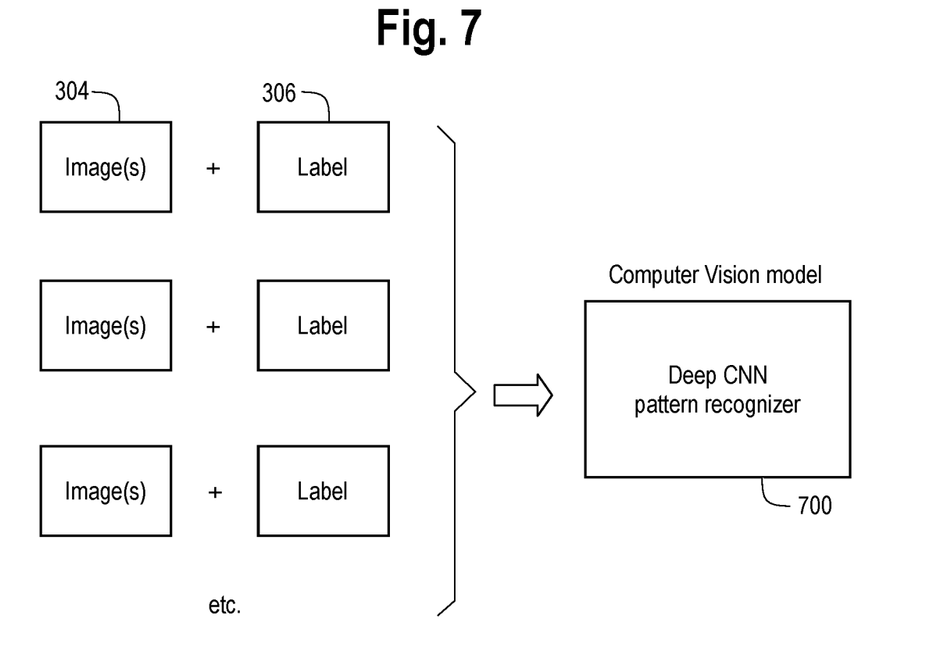
FIG. 7 is an illustration of a method of training a computer vision model (e.g., a deep convolutional neural network pattern recognizer) from a set of medical images and associated structured labels. The medical images and associated labels could for example be the medical images and labels from FIG. 3.

The medical images 304 with the structured labels 306 as generated by the NLP 100 of FIG. 3 are then used to train a computer vision model (pattern recognizes) to assign or replicate the structured labels to medical images based on image pixels alone. In particular, the training of a computer vision model 700 will be described in FIG. 7. In this example, the computer vision model 700 is in the form of a deep convolutional neural network. The computer vision model can be implemented in several different configurations. In general, deep convolutional neural network pattern recognizers, of the type used in FIG. 7, are known in the art of pattern recognition and machine vision, and therefore a detailed description thereof is omitted for the sake of brevity. One implementation is Inception-v3 deep convolutional neural network architecture, which is described in the scientific literature. See the following references, the content of which is incorporated by reference herein: C. Szegedy et al., *Going Deeper with Convolutions*, arXiv:1409.4842 [cs.CV] (September 2014); C. Szegedy et al., *Rethinking the Inception Architecture for Computer Vision*, arXiv:1512.00567 [cs.CV] (December 2015); see also US patent application of C. Szegedy et al., "*Processing Images Using Deep Neural Networks*", Ser. No. 14/839,452 filed Aug. 28, 2015, A fourth generation, known as Inception-v4 is considered an alternative architecture for the computer vision model. See C. Szegedy et al., *Inception-v4, Inception-ResNet and the Impact of Residual Connections on Learning*, arXiv: 1602.0761 [cs.CV] (February 2016). See also US patent application of C. Vanhoucke, "Image Classification Neural Networks", Ser. No. 15/395,530 filed Dec. 30, 2016. The description of the convolutional neural networks in these papers and patent applications is incorporated by reference herein.

Another alternative for the computer vision model is described in the paper of X. Wang et al., *ChestX-ray8: Hospital-scale Chest X-ray Database and Benchmarks on Weakly-Supervised Classification and Localization of Common Thorax Diseases*, arXiv:1705.02315v5 [cs.CV] (December 2017), the content of which is incorporated by reference.

For training of the computer vision model 700, we use the images 304 of FIG. 3 and labels generated by the convolutional neural network 100 as explained in FIG. 3. In essence, by training on this body of medical images 304 and associated structured labels 306 as shown in FIG. 7, the computer vision model 700 is able to take input images (pixel data alone) and generate structured labels. In other words, the computer vision model does not need associated free-text reports in order to generate structured labels. Rather, it can generate the labels on its own. So, referring now to FIG. 8, the computer vision model 700 of FIG. 7, once trained and validated, is able to take a given input image 800, for example a chest X-ray, which is not associated with a medical report, and generate a structured label 802, for example as a digital assistant to a radiologist.

One example of how the computer vision model might be used is in the context of radiology, in a hospital or clinic environment. In one configuration, the hospital or clinic will have a computer system which is configured with the necessary hardware to implement the computer vision model 700 of FIGS. 7 and 8 (details of which are not particularly important). In another configuration, the hospital or clinic could also simply request predictions from a computer vision model that is hosted by a third party service provider, in the cloud. This way, the hospital or clinic would not need to run model inference on site, but could configure their software with an application programming interface (API) to make a call to a computer system of a service provider in the cloud which hosts the computer vision model and performs inference on an input image (chest X-ray, for example) and returns via the API a structured label.

A patient has a chest X-ray performed and the digital X-ray image is supplied as input to the computer vision model. The structured label 802 is generated and then interpreted by a radiologist. For example the label [110101] in interpreted as positive for pneumothorax, left side, severity moderate, and negative for misplaced nasogastric tube and negative for cancerous lesion or lump. The radiologist inspects the X-ray with the aid of this additional information from the computer vision model and it confirms her own findings and diagnosis. As another example, the radiologist views an X-ray and comes to an initial finding of pulmonary edema and plural effusion, but after considering the structured label [010110] indicative of cardiomegaly and negative for pulmonary edema, she reconsiders her own evaluation of the X-ray, confirms that the computer vision model has correctly evaluated the X-ray and then makes the correct entries and correct diagnosis in the patient's chart, thereby avoiding a potentially serious medical error.

One of the advantages of the system and method illustrated in this document is that it permits the training of the computer vision model 700 from a large body of medical images and associated structured labels but the labels are generated automatically and do not require extensive input via human operators. While the convolution neural network (NLP) of FIG. 3 that is used in generating such labels did make use of a corpus of medical reports with labels assigned by medical experts in initial training, this amount of human involvement is relatively minor in comparison and the methodology of this disclosure allows for the generation of a very large body of training images with structured labels, on the order of thousands or even tens of thousands, and this large body of training images helps the computer vision model achieve both generalize and avoid overfitting to training data.

Figure 9:
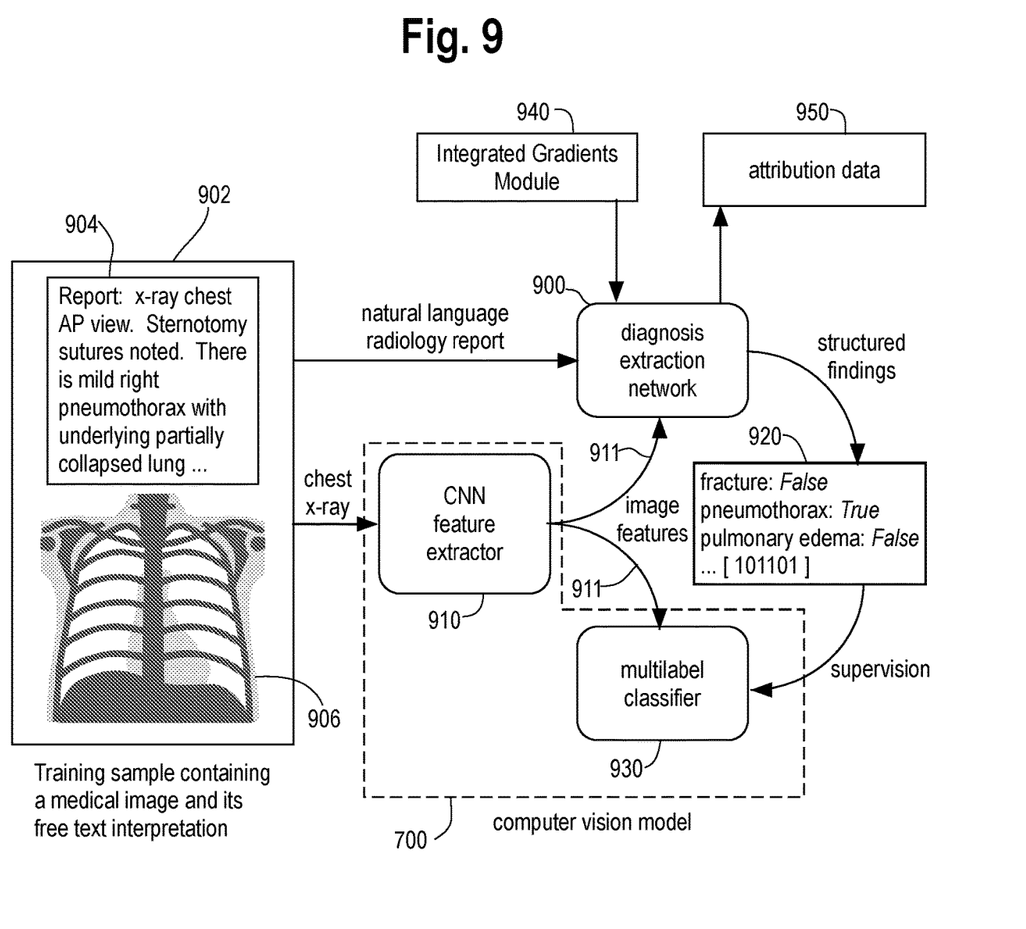
FIG. 9 is an illustration of an ensemble method of training both a computer vision model and a form of a NLP which is identified as "diagnosis extraction network" in FIG. 9.

Referring now to FIG. 9 is an illustration of an ensemble method of training both a computer vision model (700) and a diagnosis extraction network 900 which is analogous to a natural language processor (NLP) or the 1D deep convolutional neural network 100 of FIG. 2. Each training example 902, only one of which is shown, consists of a medical image 906 (e.g. a chest X-ray) and an associated free-text report 904 rendered by a radiologist. These reports are composed of unstructured natural language, and are prone to subjectivity and error. These are the lower quality, "noisy" labels. Some fraction of the training examples will have associated images that have been independently reviewed by a panel of experts and evaluated according a structured label schema or rubric (for instance, a series of binary variables indicating the presence or absence of various findings, as explained above). These labels are considered "ground-truth" labels.

The CNN feature extractor 910 is a convolutional neural network or pattern recognizer model (see examples above) that processes the medical image pixels to develop a vector representation of image features related to a classification produced by the feature extractor. The diagnosis extraction network 900 learns to extract from the report 904 clinical variables of interest using the vector representation of image features as an additional input beyond just the free-text reports 904. This allows the network 900 to not only convert the natural language into a useful format, but also correct confusion, bias or error in the original report 904. (Note that the diagnosis extraction network can be initialized with the convolutional neural network NLP model 100 (FIG. 2) that was described previously, but it is different in that it also receives the output of the CNN feature extractor 910.) The diagnosis extraction network 900 generates structured findings 910 which can be used to supervise a multi-label classifier 930 (e.g., a deep convolutional neural network pattern recognizer), which operates on the image features alone, when a ground-truth label is not available. In this way, we train a medical image diagnosis model using the abundant but noisy signal contained in the reports, relying on a smaller number of more costly ground-truth labels.

In the methodology of FIG. 9, one may optionally include an Integrated Gradients module 940 which queries the structured findings and the text in the medical reports 904 and generates attribution data 950 which can be presented to a user or stored in computer memory for evaluation of the performance of the diagnosis extraction network 900.

Figure 8:
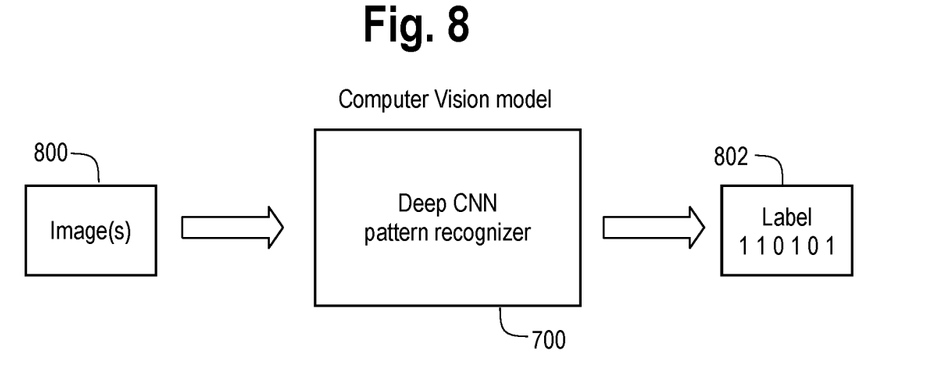
FIG. 8 is an illustration of a use of the computer visional model of FIG. 7 to generate a structured label for an input medical image, e.g., chest X-ray.

In use, after the computer vision model 700 of FIG. 9 has been trained, it can be configured in a computer system and ancillary memory and used to generate a label for an input image, e.g., chest X-ray in the manner shown in FIG. 8. In this situation, the multi-label classifier 930 generates the labels for the input image 800, even if the image is not associated with a free-text report.

Accordingly, in reference to FIG. 9, in one aspect of this disclosure we have described a machine learning system which includes a computer memory (not shown) storing a set of training data 902 in the form of a multitude of training examples, each of which comprises a free-text medical report 904 and one or more associated medical images 906. A subset of the training examples contain ground truth structured labels assigned by a medical expert. The system further includes a computer system configured to operate on each of the multitude of training examples 902, The computer system (FIG. 9) is configured as follows: it includes a) a feature extractor 910 (which may take the form of a deep convolutional neural network) receiving as input the one or more medical images 906 and generating a vector of extracted image features 911, b) a diagnosis extraction network 900 (essentially analogous to the NLP 1-D convolutional neural network 100 of FIG. 2) receiving as input a free-text medical report 904 and the vector of extracted image features 911 and generating a structured label 920; and c) an image classifier 930 (e.g., deep convolutional neural network pattern recognizer) trained on the structured labels 920 and the vector of extracted features 911. The image classifier 930 is further configured to generate a structured label for a further input medical image, for example as explained in FIG. 8.

As shown in FIG. 9, the system may optionally include an Integrated Gradients module 940 generating attribution data for the words in the free text medical reports contributing to the structured labels generated by the diagnosis extraction network 900. In one embodiment, the medical images are chest X-rays. The structured labels may take the form of binary labels for presence or absence of a medical condition or diagnosis, and/or labels for assignment of a particular diagnostic billing code. For example the medical condition could be one or more of airspace opacity (including atelactasis and consolidation), pulmonary edema, pleural effusion, pneumothorax, cardiomegaly, nodule or mass, misplaced nasogastric tube, misplaced endotracheal tube, and misplaced central venous catheter.

Data for model training complied with all requirements for disclosure and use under HIPAA and was provided with appropriate identifiers removed. Patient data was not linked to any Google user data. Furthermore, for the records used to create the models our system includes a sandboxing infrastructure that keeps each records separated from each other, in accordance with regulation, data license and/or data use agreements. The data in each sandbox is encrypted; all data access is controlled on an individual level, logged, and audited.

We claim:

1. A system for processing medical text and associated medical images comprising:
   one or more processors; and
   memory storing computer-executable instructions that, when executed by the one or more processors, cause the system to perform operations comprising:
      training a natural language processor on first training data comprising a first corpus of curated free-text medical reports each of the medical reports having one or more structured labels, to learn to read additional free-text medical reports and produce first structured labels for the additional free-text medical reports;
      generating second training data based on a second corpus of medical images, each of the medical images of the second corpus having an associated free-text medical report without a structured label, wherein the generating of the second training data comprises applying the trained natural language processor to the associated free-text medical reports of the second corpus to generate second structured labels, and wherein the second training data comprises the medical images of the second corpus and the corresponding second structured labels;
      training a computer vision model on the second training data, the computer vision model comprising:
         a feature extractor trained to generate a vector of extracted image features for each of the medical images of the second corpus, and
         an image classifier trained on the second structured labels and the vectors of extracted image features to predict an output structured label for a further input medical image, wherein the further input medical image is not associated with a medical report; and
      providing the trained computer vision model.

2. The system of claim 1, wherein the computer vision model is configured to provide, with the predicted output structured label, words or phrases based on an Integrated Gradients algorithm that assigns attribution to the words or phrases that contribute to the output structured label.

3. The system of claim 2, further comprising a workstation having a display for displaying both the further input medical image and the words or phrases that contribute to the output structured label.

4. The system of claim 1, wherein the medical images comprise chest X-rays.

5. The system claim 1, wherein the structured labels comprise labels for presence or absence of a medical condition, and/or labels for assignment of a particular diagnostic billing code.

6. The system of claim 5, wherein the medical condition comprises at least one of airspace opacity, pulmonary edema, pleural effusion, pneumothorax, cardiomegaly, nodule or mass, misplaced nasogastric tube, misplaced endotracheal tube, misplaced central venous catheter.

7. The system of claim 1, further comprising:
receiving the further input medical image not associated with a free-text medical report; and
applying the trained computer vision model to predict the output structured label based on the further input medical image.

8. A method for processing medical text and associated medical images comprising:
training a natural language processor on first training data comprising a first corpus of curated free-text medical reports each of which having one or more structured labels assigned by an medical expert, the natural language processor trained to learn to read additional free-text medical reports and produce first structured labels for the additional free-text medical reports;
generating second training data based on a second corpus of medical images, each of the medical images of the second corpus having an associated free-text medical report without a structured label, wherein the generating of the second training data comprises applying the trained natural language processor to the associated free-text medical reports of the second corpus to generate second structured labels, and wherein the second training data comprises the medical images of the second corpus and the corresponding second structured labels; and
training a computer vision model on the second training data, the computer vision model comprising:
a feature extractor trained to generate a vector of extracted image features for each of the medical images of the second corpus, and
an image classifier trained on the second structured labels and the vectors of extracted image features to predict an output structured label for a further input medical image, wherein the further input medical image is not associated with a medical report; and
providing the trained computer vision model.

9. The method of claim 8, wherein the computer vision model is configured to provide, with the predicted output structured label, words or phrases comprises applying an Integrated Gradients algorithm to assign attribution to the words or phrases that contribute to the output structured label.

10. The method of claim 9, further comprising displaying both the further input medical image and the words or phrases that contribute to the output structured label on a workstation.

11. The method of claim 8, wherein the medical images comprise chest X-rays.

12. The method of claim 8, wherein the structured labels comprise labels for presence or absence of a medical condition, and/or labels for assignment of a particular diagnostic billing code.

13. The method of claim 12, wherein the medical condition comprises at least one of airspace opacity, pulmonary edema, pleural effusion, pneumothorax, cardiomegaly, nodule or mass, misplaced nasogastric tube, misplaced endotracheal tube, misplaced central venous catheter.

14. The method of claim 8, further comprising:
receiving the further input medical image not associated with a free-text medical report; and
applying the trained computer vision model to predict the output structured label based on the further input medical image.

15. The method of claim 8, wherein the natural language processor is trained in an ensemble manner with the computer vision model, wherein the ensemble training comprises:
receiving, by the natural language processor, the free-text medical reports of the second corpus and the vector of extracted image features for each of the medical images output by the feature extractor;
generating, by the natural language processor, one or more structured findings corresponding to each of the medical images; and
providing the one or more structured findings to the image classifier for the training of the computer vision model.

16. A machine learning system comprising, in combination,
a computer memory storing first training data comprising a first corpus of curated free-text medical reports each of the medical reports having one or more structured labels; and
a computer system configured to operate on each of the multitude of training examples, and wherein the computer system is configured as:
a) a natural language processor receiving as input the first training data and training to read additional free-text medical reports and produce first structured labels for the additional free-text medical reports;
b) the trained natural language processor receiving a second corpus of medical images, each of the medical images of the second corpus having an associated free-text medical report without a structured label, and outputting second structured labels for the associated free-text medical reports;
c) a feature extractor receiving as input the medical images of the second corpus and generating a vector of extracted image features from the medical images of the second corpus; and
d) an image classifier trained on vectors of extracted features produced by the feature extractor from the medical images of the second corpus and corresponding second structured labels, wherein the image classifier is further configured to generate an output structured label for a further input medical image from a further feature vector generated by the feature extractor from the further input medical image.

17. The system of claim 16, wherein the image classifier is configured to provide, with the output structured label, words or phrases based on an Integrated Gradients algorithm to generate attribution data for the words or phrases that contribute to the output structured label.

18. The system of claim 16, wherein the medical images comprise chest X-rays.

19. The system of claim 16, wherein the structured labels comprise labels for presence or absence of a medical condition, and/or labels for assignment of a particular diagnostic billing code.

20. The system of claim 19, wherein the medical condition comprises at least one of airspace opacity, pulmonary edema, pleural effusion, pneumothorax, cardiomegaly, nodule or mass, misplaced nasogastric tube, misplaced endotracheal tube, misplaced central venous catheter.

21. The system of claim 16, wherein a subset of the first training data comprise ground truth structured labels assigned by a medical expert, and wherein the ground truth structured labels, the structured label generated by the diagnosis extraction network, and the output structured label, are binary strings, wherein each binary digit of each binary string indicates a presence or an absence of a medical condition.

\* \* \* \* \*